US00PP27564P3

(12) United States Plant Patent
Rebello

(10) Patent No.: US PP27,564 P3
(45) Date of Patent: Jan. 17, 2017

(54) ***XEROCHRYSUM* PLANT NAMED 'BONDRE 1051'**

(50) Latin Name: *Xerochrysum bracteatum*
Varietal Denomination: Bondre 1051

(71) Applicant: Bonza Botanicals Pty., Ltd., Yellow Rock, NSW (AU)

(72) Inventor: Shaun Rebello, Blair Athol (AU)

(73) Assignee: Bonza Botanicals Pty., Ltd., Yellow Rock, NSW (AU)

( * ) Notice: Subject to any disclaimer, the term of this patent is extended or adjusted under 35 U.S.C. 154(b) by 114 days.

(21) Appl. No.: 14/544,550

(22) Filed: Jan. 20, 2015

(65) Prior Publication Data

US 2016/0212902 P1 Jul. 21, 2016

(51) Int. Cl.
*A01H 5/02* (2006.01)

(52) U.S. Cl.
USPC ..... Plt./359

(58) Field of Classification Search
USPC ..... Plt./359, 263.1
See application file for complete search history.

(56) References Cited

PUBLICATIONS

Ball Flora Plant Dreamtime Jumbo Rose Bracteantha, retrieved on Jul. 7, 2016, retrieved from the Internet at <http://www.ballfloraplant.com/series_info.aspx?phid=031902470033239> 1 page.*

Canadian Food Inspection Agency for 'Bondre 1051' Application No. 2014-11-13, retrieved on Jul. 7, 2016, retrieved from the Internet at <http://www.inspection.gc.ca/english/plaveg/pbrpov/cropreport/stfl/app00009827e.shtml> 2016, 4 pp.*

* cited by examiner

*Primary Examiner* — June Hwu
(74) *Attorney, Agent, or Firm* — Audrey Charles

(57) ABSTRACT

A new and distinct cultivar of *Xerochrysum* plant named 'Bondre 1051', characterized by its rose-colored inflorescences, dark green-colored foliage, and moderately vigorous, compact-mounded growth habit, is disclosed.

1 Drawing Sheet

Latin name of genus and species of plant claimed: *Xerochrysum bracteatum.*

Variety denomination: 'Bondre 1051'.

BACKGROUND OF THE INVENTION

The present invention relates to a new and distinct cultivar of *Xerochrysum* plant botanically known as *Xerochrysum bracteatum* and hereinafter referred to by the cultivar name 'Bondre 1051'.

The new cultivar originated in a controlled breeding program in Yellow Rock, New South Wales, Australia during August 2009. The objective of the breeding program was the development of *Xerochrysum* cultivars with unique flower coloration, and compact, upright-mounded growth habit.

The new *Xerochrysum* cultivar is the result of cross-pollination. The female (seed) parent of the new cultivar is the proprietary *Xerochrysum bracteatum* breeding selection coded 09-20, not patented, characterized by its medium reddish-orange colored inflorescences, medium green-colored foliage, and moderately vigorous, upright growth habit. The male (pollen) parent of the new cultivar is the proprietary *Xerochrysum bracteatum* breeding selection coded 09-72, not patented, characterized by its red-colored inflorescences, medium green-colored foliage, and vigorous, mounded growth habit. The new cultivar was discovered and selected as a single flowering plant within the progeny of the above stated cross-pollination during March 2010 in a controlled environment in Yellow Rock, New South Wales, Australia.

Asexual reproduction of the new cultivar by terminal stem cuttings since March 2010 in Yellow Rock, New South Wales, Australia, Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Bondre 1051' as a new and distinct cultivar of *Xerochrysum* plant:

1. Rose-colored inflorescences;
2. Dark green-colored foliage; and
3. Moderately vigorous, compact-mounded growth habit.

Plants of the new cultivar differ from plants of the female and male parents primarily in having a different bract color and in having a more compact growth habit.

Of the many commercially available *Xerochrysum* cultivars, the most similar in comparison to the new cultivar is 'Helica Purple Improved' not patented. However, in comparison, plants of the new cultivar differ from plants of 'Helica Purple Improved' in at least the following characteristics:

1. Plants of the new cultivar have larger inflorescences than plants of 'Helica Purple Improved';
2. Plants of the new cultivar have a bract color different from plants of 'Helica Purple Improved'; and 3. Plants of the new cultivar have more branches than plants of 'Helica Purple Improved'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Bondre 1051'. The plants were grown in 4-inch pots for 7 weeks in a greenhouse in West Chicago, Ill. Plants were given one pinch at transplant.

DETAILED BOTANICAL DESCRIPTION

Figure 1:
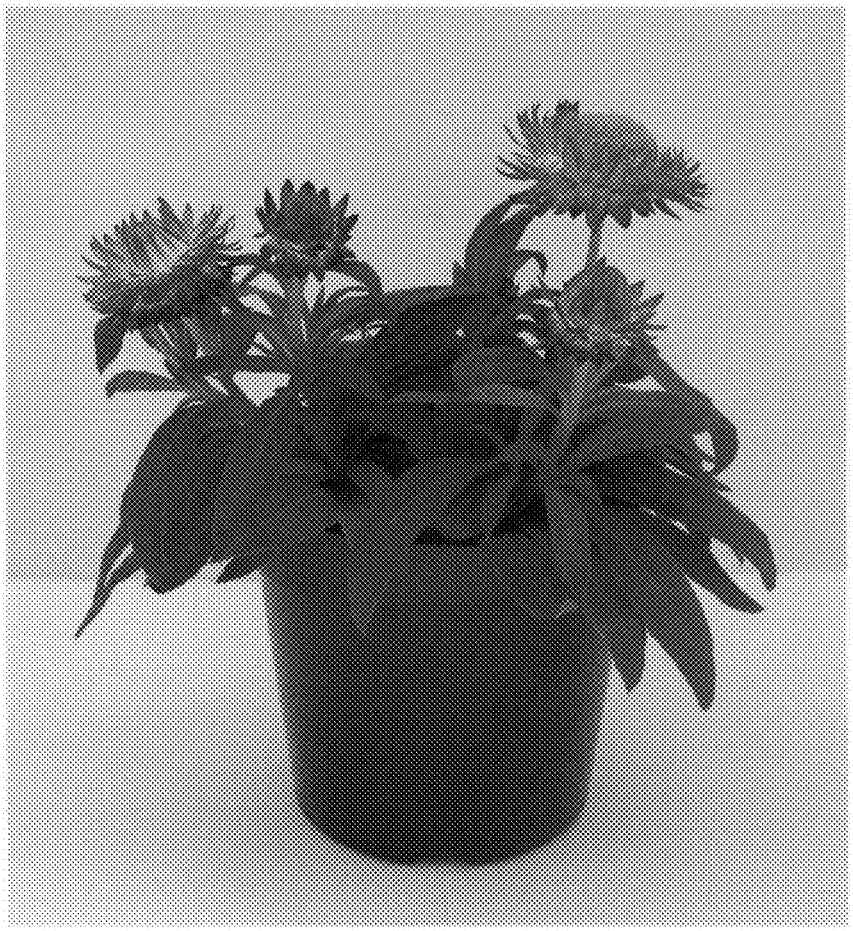
FIG. 1 illustrates a side view of the overall growth and flowering habit of 'Bondre 1051'.
Figure 2:
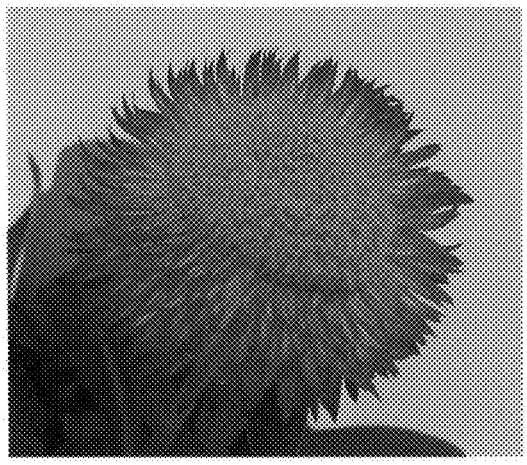
FIG. 2 illustrates a close-up view of an individual inflorescence of 'Bondre 1051'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in October 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 7 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Xerochrysum bracteatum* cultivar Bondre 1051.

Parentage:

*Female parent.*—Proprietary *Xerochrysum bracteatum* breeding selection coded 09-20, not patented.

*Male parent.*—Proprietary *Xerochrysum bracteatum* breeding selection coded 09-72, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous, fine.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, compact-mounded.

*Size.*—Height from soil level to top of plant plane: Approximately 12.5 cm. Width: Approximately 18.0 cm.

*Branching habit.*—Freely branching, pinching enhances lateral branching. Quantity of main branches per plant: Approximately 4.

*Branch.*—Strength: Strong. Length to base of peduncle: Approximately 4.0 cm. Diameter: Approximately 3.0 mm. Length of central internode: Approximately 5.0 mm. Texture: Densely pubescent. Color of young and mature stems: 144D.

Foliage description:

*General description.*—Quantity of leaves per main branch: Approximately 7. Fragrance: Slight. Form: Simple. Arrangement: Alternate.

*Leaves.*—Aspect: Acute angle to stem, tips turn downward with age. Shape: Narrowly elliptic. Margin: Entire. Apex: Acuminate. Base: Sessile. Venation pattern: Pinnate. Length of mature leaf: Approximately 7.5 cm. Width of mature leaf: Approximately 1.5 cm. Texture of upper surface: Moderately pubescent. Texture of lower surface: Sparsely pubescent. Color of upper surface of young foliage: 137A with indistinguishable venation except for midvein of 145B. Color of lower surface of young and mature foliage: Closest to 137B with indistinguishable venation except for midvein of 145B. Color of upper surface of mature foliage: Closest to N137A with 139A and indistinguishable venation except for midvien of 145B.

Flowering description:

*Flowering habit.*—'Bondre 1051' is freely flowering under outdoor growing conditions with substantially continuous blooming from spring through autumn and year-round in greenhouse environment.

*Lastingness of individual inflorescence on the plant.*—Approximately 2 to 3 weeks.

Inflorescence description:

*General description.*—Type: Composite. Persistent. Shape: Hemispherical when involucral bracts are fully expanded. Aspect: Facing outward or upward held above the foliage. Arrangement: Terminal, solitary. Disc florets and involucral bracts develop acropetally on a capitulum. Fragrance: Slight. Quantity per plant: Approximately 3. Diameter: Approximately 4.5 cm. Depth: Approximately 2.2 cm.

*Peduncle.*—Strength: Strong. Aspect: Erect. Length: Approximately 7.5 cm. Diameter: Approximately 3.0 mm. Texture: Tomentose. Color: 144B.

*Bud.*—Rate of opening: Generally takes 14 to 21 days for bud to progress from first color to fully open flower. Quantity per plant: Approximately 1.

*Bud just before opening.*—Shape: Ovoid. Length: Approximately 1.3 cm. Diameter: Approximately 1.1 cm. Color: 187A and 187B.

*Involucral bracts.*—Quantity per inflorescence: Approximately 300. Arrangement: Imbricate in approximately 15 whorls. Aspect: Initially at acute angle to disc, becoming perpendicular to downward turning at maturity. Shape: Lanceolate, slightly cupped with sides turned upward. Margin: Entire. Apex: Acute. Base: Truncate. Length of outermost: Approximately 1.6 cm. Length of innermost: Approximately 8.0 mm. Width of outermost: Approximately 5.0 mm. Width of innermost: Approximately 1.0 mm. Texture of upper and lower surfaces: Glabrous, papery. Color of upper surface when first and fully open: Base of NN155D transitioning through 71B to 71A at apex. Color of lower surface when first and fully open: Base of NN155D transitioning through 187D to 187B at apex.

*Disc florets.*—Quantity per inflorescence: Numerous, greater than 1,000. Arrangement: Massed in center of inflorescence. Shape: Tubular with an outer whorl of approximately 20 feather-like filaments, approximately 6.0 mm in length and NN155A in color. Margin: Entire. Apex: Five acute tips. Base: Fused. Length: Approximately 1.0 cm. Diameter at apex: Approximately 1.0 mm. Diameter at base: Less than 1 mm. Texture: Glabrous. Color when fully open: 21A transitioning through NN155D with faint overlay of 21A to a base of NN155D.

*Disc.*—Diameter: Approximately 2.3 cm. Depth: Approximately 1.0 cm.

*Receptacle.*—Shape: Flat. Diameter: Approximately 2.2 cm. Color: 155C.

*Reproductive organs.*—Androecium: Stamen quantity: 5 per floret, fused around the style. Stamen length: Approximately 7.0 mm. Anther shape: Linear. Anther length: Approximately 3.0 mm. Anther color: 14A. Pollen amount: Moderate. Pollen color: 14B. Gynoecium: Pistil quantity: 1 per floret. Pistil length: Approximately 1.0 cm. Stigma shape: Bi-parted. Stigma length: Approximately 1.0 mm. Stigma color: 21A. Style length: Approximately 8.0 mm. Style color: Colorless, opaque. Ovary length: Approximately 1.0 mm. Ovary color: NN155D.

Seed and fruit production: Neither seed nor fruit production has been observed.

Disease and pest resistance: Resistance to pathogens and pests common to *Xerochrysum* has not been observed.

What is claimed is:

1. A new and distinct cultivar of *Xerochrysum* plant named 'Bondre 1051', substantially as herein illustrated and described.

* * * * *